:::
United States Patent [19]

Klausz

[11] 4,343,995
[45] Aug. 10, 1982

[54] METHOD AND APPARATUS FOR AUTOMATICALLY CENTERING AN OBJECT FOR TOMODENSITOMETRIC EXAMINATION

[75] Inventor: Remy Klausz, Paris, France

[73] Assignee: Compagnie Generale de Radiologie, Paris, France

[21] Appl. No.: 58,980

[22] Filed: Jul. 20, 1979

[30] Foreign Application Priority Data

Jul. 27, 1978 [FR] France .................. 78 22268

[51] Int. Cl.$^3$ .................. A61B 6/00; A61B 6/02; G06F 15/42
[52] U.S. Cl. .................. 278/21; 250/491.1
[58] Field of Search .................. 250/445 T, 491

[56] References Cited

U.S. PATENT DOCUMENTS 4,195,229  3/1980  Susuki .................. 250/445 T
4,278,888  7/1981  Wagner .................. 250/491

Primary Examiner—Alfred E. Smith
Assistant Examiner—T. N. Grigsby
Attorney, Agent, or Firm—Roland Plottel

[57] ABSTRACT

A tomodensitometric apparatus for the radiological examination of an object by relative rotation with respect to said object of a fixed array consisting of a source of penetrating radiation and a plurality of detectors disposed along a line. In order to correctly position the object in the center of the radiation field prior to the examination and without subjecting the object to a dose of test radiation, the invention provides a movable screen which is placed between the source and the object to be examined. The dimensions of the screen are such as to prevent the radiation emanating from the source from reaching any but at least one of the two outermost-lying detectors in the line of detectors. When the array is rotated in a test cycle, the signals from the one or two outermost detectors are received by a suitably programmed computer which generates a displacement schedule that is transmitted to the controller and displaces the object in the direction necessary to move it to the center of the radiation field.

5 Claims, 1 Drawing Figure

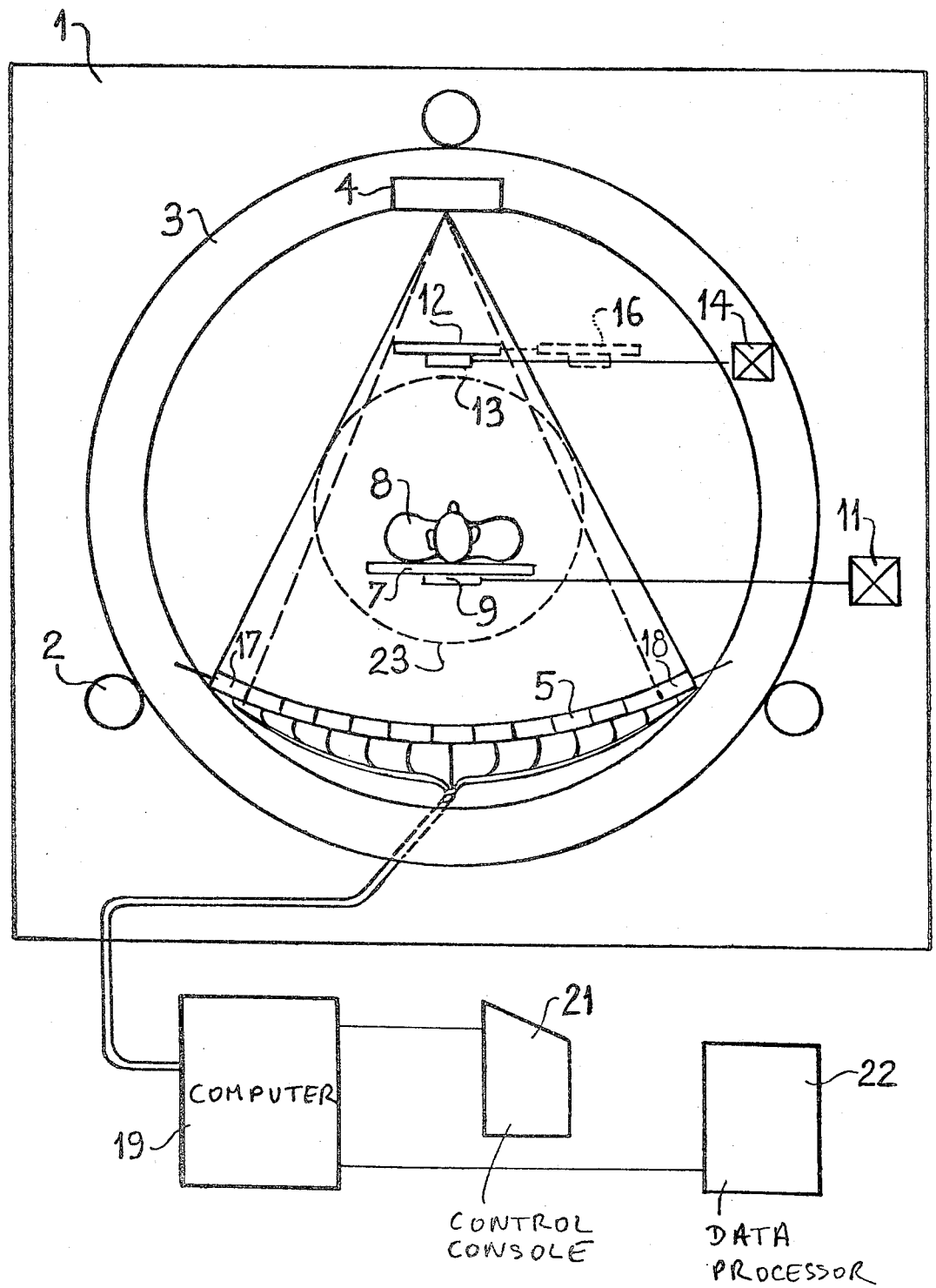

METHOD AND APPARATUS FOR AUTOMATICALLY CENTERING AN OBJECT FOR TOMODENSITOMETRIC EXAMINATION

FIELD OF THE INVENTION

The invention relates to apparatus for examining objects by means of penetrating radiation, for example X-rays. More particularly, the invention relates to scanning tomodensitometric apparatus in which the degree of beam interception is correlated with the angle of examination by associated computers.

BACKGROUND OF THE INVENTION

A tomodensitometric apparatus usually includes a source of radiation which emits the radiation in a diverging, fan-shaped beam which defines a sector of the tomographic plane in which the object to be examined is placed. The source and the detectors of the radiation are attached to a movable support which is capable of rotation about an axis which is perpendicular to the tomographic plane and is located substantially in the center of the object to be examined. The varying signals emitted by each of the plurality of detectors are received by a suitably programmed computer during the cycle of rotation. The computer processes these signals and derives from them information regarding the degree of absorption of radiation and forms an image of the examined object on the basis of the data.

In order for the calculations and the processing to be exact, i.e., to correspond to the objects actually examined, it is indispensable that the totality of the object be irradiated during the entire cycle, i.e., that all of the points of the object to be examined lie at all times within the sector defined by the source and the detectors. The foregoing condition may be expressed by saying that the object to be measured must lie within a so-called field of measurement, i.e., a circle whose periphery is defined by the envelope of rays intercepted from the source by the detectors lying at the extreme ends of the array of detectors as traced out during the rotation of the assembly. If the object to be examined did not lie inside such a circle, then at some times during the cycle of examination, parts of the object would not be measured, leading to an erroneous result. It is thus of the utmost importance to place the object at the interior of the aforementioned circle, an action which might be termed "centering".

This act of centering could be performed by simulating the measuring field with mechanical openings or by the generation of a luminous pattern with which the object to be examined could be aligned. However, in such a case these centering means would also have to be correctly centered on the measuring field, which presupposes lengthy preliminary operations and considerable care. Furthermore, the use of such systems tends to be complicated and slow. The object to be examined could also be correctly centered by means of light sources and light detectors in the optical part of the spectrum but such mechanisms would also require additional associated electronic circuits, either for use by the operator of the machine or for use by the computer.

In principle, it would even be possible to perform a test cycle using penetrating radiation and to make necessary corrections if the object were not correctly centered. However, it is to be noted that this procedure is definitely excluded due to the detrimental effects of the additional radiation received by the patient or body to be examined in such a test cycle.

OBJECT AND SUMMARY OF THE INVENTION

It is thus a principal object of the present invention to provide a method and an apparatus for correctly placing and centering an object to be examined within the field of measurement of a tomodensitometric apparatus without the necessity for relatively complicated electronic or mechanical assemblies as described above. This object is attained according to the invention in a method which uses the radiation detectors at the extreme ends of the detector array for determining if the object to be examined blocks the rays they receive from the source. If such is the case, the detectors generate attenuated signals which are used by the computer to initiate an automatic displacement of the object to be examined.

The method according to the invention more particularly involves the following steps. An opaque screen is placed between the source of penetrating radiation and the object to be examined. The screen has an extent which prevents all but the rays intercepted by the detectors at the extreme ends of the array from reaching the object to be examined. The tomodensitometer is then exercised through one cycle of examination, i.e., it is rotated through 360°. If the two extreme detectors which receive radiation that passes by the opaque screen indicate no obstruction, the object to be examined is assumed to be correctly centered. If, on the other hand, one or the other of these detectors shows an attenuation of the beam, the object is assumed to extend beyond the field of measurement and an automatic correction of its position is effected by the computer.

The method according to the invention may be used with different types of apparatus, i.e., tomodensitometers which translate and rotate as well as those which only rotate. However, the method is particularly adaptable to apparatus having fan-shaped beams which only rotate.

The invention includes the provision of an apparatus for carrying out the aforementioned method. This apparatus can be adapted to various types of tomodensitometers. In particular however, it is applicable to tomodensitometers having fan-shaped beams in which the source and the detectors rotate about an axis.

The invention will be better understood and the application of the method to an apparatus will be illustrated in the subsequent detailed description of a preferred exemplary embodiment taken in conjunction with the drawing.

BRIEF DESCRIPTION OF THE DRAWING

The single FIGURE of the drawing is an end view of a rotating tomodensitometer according to the invention.

DESCRIPTION OF THE PREFERRED EMBODIMENT

Turning now to the FIGURE, there will be seen a frame or housing 1 in which is disposed a rotatable support 3 which turns, for example, on three rollers 2. Mounted on the support frame 3 is a source of radiation 4 and an extended array of detectors 5. The interior of the housing has provision for permitting the passage of a support 7 on which the object to be examined 8 is placed during the examination. The support 7 is attached to a mechanism 9 attached to the housing 1 and capable of being displaced by a control element 11 in any desirable direction within the plane of the single FIGURE.

It is a principal characteristic of the present invention to provide a screen 12 which is opaque to the radiation from the source 4 and which is mounted on a movable mechanism 13 attached to the frame 3. An actuator 14 permits the displacement of the screen 12 between at least two positions, a first centered position such as indicated by the numeral 12 and a second standby position 16 shown in dashed lines. As illustrated, the lateral dimensions of the screen 12 are such that in its centered position 12, it prevents all but the extreme lateral rays from continuing beyond the screen and permits only the passage of the rays which would normally strike the end detectors 17 or 18. It is also possible and sufficient according to the invention if only one detector 17 or 18 is permitted to receive radiation when the screen 12 is in its centered position.

The electrical signal outputs of the array of detectors 5 are fed to a computer 19 which may be programmed either internally or by a control console 21. The computer results are then sent to a data processor or display console 22.

The tomodensitometer has an automatic centering feature which operates as follows. When the source 4 is energized and the screen 12 is in its centered obscuring position, the support frame 3 is rotated. During the rotation, the rays which impinge on the detectors 17 and 18 define a field of measurement which is shown in the FIGURE by the dashed circle 23. In order to obtain correct and consistent results, the object to be examined must lie within this circle during the entire cycle of rotation. This condition will definitely be met if neither of the detectors 17 or 18 is obscured by any part of the object to be examined during the test rotation. If a part of the object obscures one of the detectors during the rotation, the signal from that detector is changed so that the computer 19, under the built-in program or the program received from the control console 21, calculates from these signals as well as from the prevailing angular position of the support frame 3 in what direction and to what extent the object 8, i.e., the support 7, must be moved to prevent the interception of the beam by the object 8. If neither of the detectors 17 or 18 is obscured at all during the test cycle, then the position is assumed to be correct.

The presence of the opaque screen 12 during the test cycle in the center of the beam from the source 4 insures that the required information which is obtained from the end detectors 17 and 18 does not entail unnecessary irradiation of the object to be examined.

The steps performed by the apparatus in its automatic centering function are thus as follows.

1. The opaque screen 12 is centered, i.e., placed between the source 4 and the object 8,
2. the computer is programmed and/or activated, and
3. the test rotation cycle is initiated.

The calculated displacements based on the signals from the detectors 17 and 18 are sent to the processor 22 which directly actuates the control element 11 that automatically causes the proper displacement of the support 7 as calculated by the computer 19.

Inasmuch as the detectors are placed symmetrically with respect to the rotational axis of the support frame 3, the field circle 23 is defined by either one of the rays which impinge on the detectors 17 and 18, respectively, during a complete rotation. Thus a variant embodiment of the invention would provide that the screen 12 obscures all radiation except that which would impinge on one or the other of the detectors 17 or 18.

In some tomodensitometers, provision is made for altering the size of the field of measurement. This alteration may be obtained either by opening and closing the angular extent of the fan-shaped beam from the source 4 or by changing the position of the source with respect to the center of rotation of the support frame 3. In either case, the obscuration angle, i.e., the shadow angle, of the screen 12 could be changed either by changing the lateral extent of the screen 12, for example by having a number of screens of different widths or by changing the radial position of the screen 12 with respect to the source. The latter motion could be performed by a suitably adapted control element 14.

The foregoing relates to preferred exemplary embodiments of the invention, it being understood that other embodiments and variants thereof are possible within the spirit and scope of the invention.

What is claimed and desired to be secured by Letters Patent of the United States is:

1. A method for positioning an object to be examined in a tomodensitometric apparatus, said apparatus including a source of a fan-shaped beam of radiation and a plurality of radiation detectors disposed along a line, said source and said detectors being located on a rotatable mount which is capable of rotation about an axis normal to a plane defined jointly by said source and said detectors, said apparatus further including a support for said object to be examined, said support being capable of motion in any direction as urged by a control element under the control of a controller which receives control information from a computer programmed by a control console and by an internal program and connected to receive signals from said detectors, and wherein, according to the invention, said method comprises the steps of:
   placing said object on said movable support;
   positioning between said object and said source an opaque screen which prevents the radiation from said source from striking any except at least one of the two outermost-lying detectors along said line;
   programming said computer so as to generate a control schedule which defines the direction and magnitude of displacements to be given to said movable support in dependence of the degree of attenuation of signals from said at least one of the two outermost-lying detectors during a rotation of said rotatable mount in a test cycle; and
   executing a test cycle in which said rotatable mount is turned through one revolution; whereby said object is centered within the effective beam of said source for all relative angular positions thereof.

2. A tomodensitometric apparatus including a source of a fan-shaped beam of radiation and a plurality of radiation detectors, disposed along a line, said source and said detectors being located on a rotatable mount which is capable of rotation about an axis normal to a plane defined jointly by said source and said detectors, said apparatus further including a support for said object to be examined, and a controller which receives control information from a computer programmed by a control console and by an internal program and connected to receive signals from said detectors, the improvement according to the invention comprising:
   a screen which is opaque to the radiation from said source and is attached to a movable mechanism coupled to an actuator so as to be capable of being placed in a central, obscuring position between said source and said object, said screen being of such dimensions as to prevent the radiation from said source from striking any except at least one of the two outermost-lying detectors on said line.

3. An apparatus according to claim 2, wherein said movable mechanism includes a provision for holding opaque screens of varying size.

4. An apparatus according to claim 2, wherein said movable mechanism includes a capability of moving said screen radially to and from said source.

5. An apparatus according to claim 2, wherein said support for said object is capable of motion in any direction as urged by a control element under the control of said controller.

* * * * *